US006245332B1

(12) United States Patent
Butcher et al.

(10) Patent No.: US 6,245,332 B1
(45) Date of Patent: Jun. 12, 2001

(54) MODULATION OF SYSTEMIC MEMORY T CELL TRAFFICKING

(75) Inventors: Eugene C. Butcher, Portola Valley; James J. Campbell, Palo Alto, both of CA (US); Lijun Wu, Reading; James B. Rottman, Sudbury, both of MA (US)

(73) Assignees: The Board of Trustees of the Leland Stanford Junior University, Palo Alto, CA (US); LeukoSite, Inc., Cambridge, MA (US)

( * ) Notice: Subject to any disclaimer, the term of this patent is extended or adjusted under 35 U.S.C. 154(b) by 0 days.

(21) Appl. No.: 09/232,878

(22) Filed: Jan. 15, 1999

(51) Int. Cl.[7] .................. A61K 39/38; A61K 39/395; A61K 38/00; A61K 45/00; G01N 33/53

(52) U.S. Cl. ............. 424/184.1; 424/85.1; 424/130.1; 424/139.1; 424/141.1; 424/145.1; 514/1; 514/2; 514/12

(58) Field of Search ................ 435/7.1, 7.24; 424/130.1, 139.1, 141.1, 145.1, 184.1, 85.1; 514/1, 2, 12

(56) References Cited

U.S. PATENT DOCUMENTS 5,932,703 * 8/1999 Godiska et al. .

FOREIGN PATENT DOCUMENTS

| 0 860 446 | 8/1998 | (EP) . |
| WO 96/23068 | 8/1996 | (WO) . |
| WO 98/44953 | 10/1998 | (WO) . |

OTHER PUBLICATIONS

Andrew et al. J. Immunology 161:5027–5083, 1998.*
Sallusto et al. Journal of Experimental Medicine, 187:875–883, Mar. 1998.*
Bonnechi, et al., "Differential Expression of Chemokine Receptors and Chemotactic Responsiveness of Type 1T Helper Cells (Th 1s) and Th2s," *J. Exp. Med.* (Jan. 5, 1998) vol. 187, No. (1): 129–134.
Durig, et al., "Expression of Macrophage Inflammatory Protein–1α Receptors In Human CD34+ Hematopoietic Cells And Their Modulation by Tumor Necrosis Factor–α an Interferon–γ," *Blood* (Nov. 1, 1998) vol. 92, No. (9): 3073–3081.
Imai, et al., "Macrophage–Derived Chemokine Is A Functional Ligand For The CC Chemokine Receptor 4*," *J. Biol. Chem.* (Jan. 16, 1998) vol. 273, No. (1): 1764–1768.
Imai, et al., "The T Cell–Directed CC Chemokine TARC Is A Highly Specific Biological Ligand For CC Chemokine Receptor 4*," *J. Biol. Chem.* (Jun. 16, 1997) vol. 272, No. (23): 15036–15042.
Meyer, et al., "Cloning and Characterization of a Novel Murine Macrophage Inflammatory Protein–1α Receptor*," *J. Biol. Chem.*, (Jun. 14, 1996) vol. 271, No. (24): 14445–14451.

Power, et al., "Molecular Cloning and Functional Expression of a Novel CC Chemokine Receptor cDNA From A Human Basophilic Cell Line," *J. Biol. Chem.*, (Aug. 18, 1995) vol. 270, No. (33): 19495–19500.
Catalog of Santa Cruz Biotechnology, Inc., Research Antibodies 97/98: 319–320.
Youn, et al., "Molecular Cloning And Characterization of A cDNA, CHEMR1, Encoding A Chemokine Receptor With Homology To The Human C–C Chemokine Receptor, CCR–4," A *Blood*, (Jun. 15, 1997) vol. 89, No. (12):4448–4460.
Genebank Accession No. X85740, Locus HSCCCR3, "H. Sapiens mRNA for C–C Chemokine Receptor–4" (1996).
Genebank Accession No. X94151, Locus MMMIP1A2, "M. Musculus mRNA for MIP–1 Alpha Receptor 2" (1996).
Baggiolini, Marco, "Chemokines And Leuckocyte Traffic," *Nature* (Apr. 9, 1998) vol. 392:565–568.
Baggiolini, Marco, et al., "Blocking Chemokine Receptors," *J. Exp. Med.* (Oct. 20, 1997) vol. 186, No. (8):1189–1191.
Campbell, James J., et al., "6–C–kine (SLC), A Lymphocyte Adhesion–Triggering Chemokine Expressed By High Endothelium, Is An Agonist For The MIP–3β Receptor CCR&," *The Journal of Cell Biology* (May 18, 1998) vol. 141, No. (4):1053–1059.
Dutton, R.W., et al., "T Cell Memory," *Ann. Rev. Immunol.* (1998) vol. 16:201–23.
Fuhlbrigge, Robert C., et al., "Cutaneous Lymphocyte Antigen Is A Specialized Form of PSGL–1 Expressed On Skin–Homing T Cells," *Nature* (Oct. 30, 1997) vol. 389:978–981.
Tangeman, Kirsten, et al., "A High Endothelial Cell–Derived Chemokine Induces Rapid, Efficient, And Subset–Selective Arrest of rolling T Lymphocytes On A Reconstituted Endothelial Substrate[1]," *The Journal of Immunology* (1998) vol. 161:6330–6337.
Teraki Yuichi, et al., "Independent Regulation of Cutaneous Lymphocyte–Associated Antigen Expression and Cytokine Synthesis Phenotype During Human CD4+ Memory T Cell Differentiation[1]," *The Journal of Immunology* (1997) vol. 159:6018–6029.

* cited by examiner

Primary Examiner—David Saunders
Assistant Examiner—Amy Decloux
(74) Attorney, Agent, or Firm—Pamela J. Sherwood; Bozicevic, Field & Francis LLP

(57) ABSTRACT

Methods are provided to specifically modulate the trafficking of systemic memory T cells, particularly CD4+ T cells, without affecting naive T cells or intestinal memory T cells. It is shown that systemic memory T cells, which are characterized as CD45Ra−, and integrin α4β7−, express high levels of CCR4. Ligands of CCR4, such as TARC or MDC, act as an adhesion trigger, wherein upon CCR4 binding, these cells undergo integrin-dependent arrest to the appropriate vascular receptor(s). This arrest acts to localize the cells at the target site. The methods of the invention manipulate this triggering, and CCR4 mediated chemotaxis, to affect the localization of T cells in targeted tissues. In one embodiment of the invention, the active agent is a CCR4 agonist, that acts to enhance T cell localization. In an alternative embodiment, the agent is an antagonist that blocks CCR4 biological activity. An advantage of the invention is the selectivity for systemic memory T cells, without affecting native T cells or intestinal memory T cells.

15 Claims, 7 Drawing Sheets

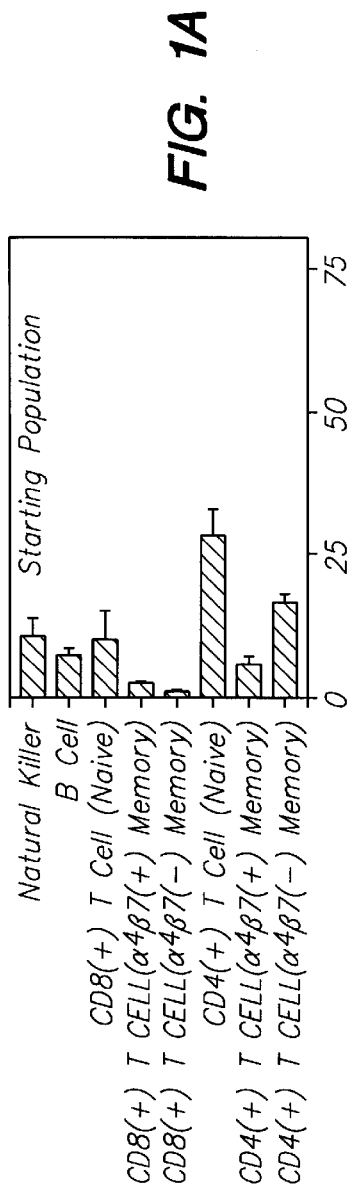
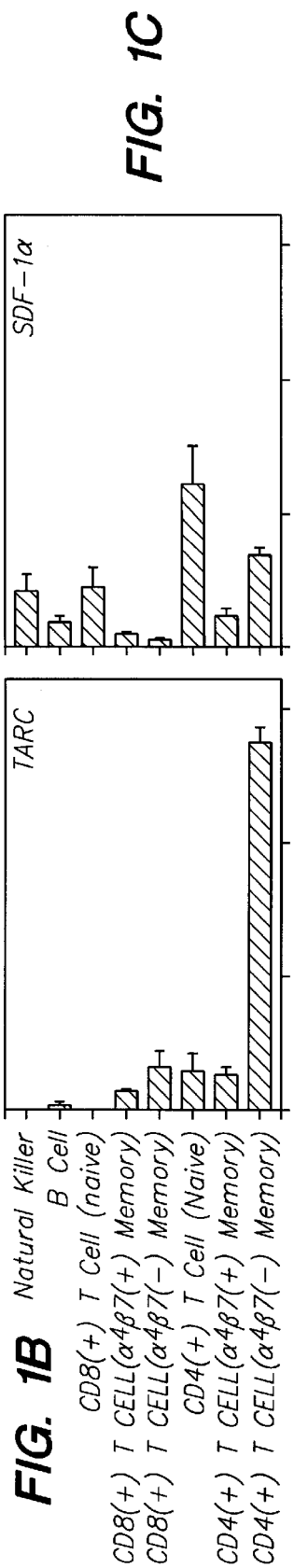
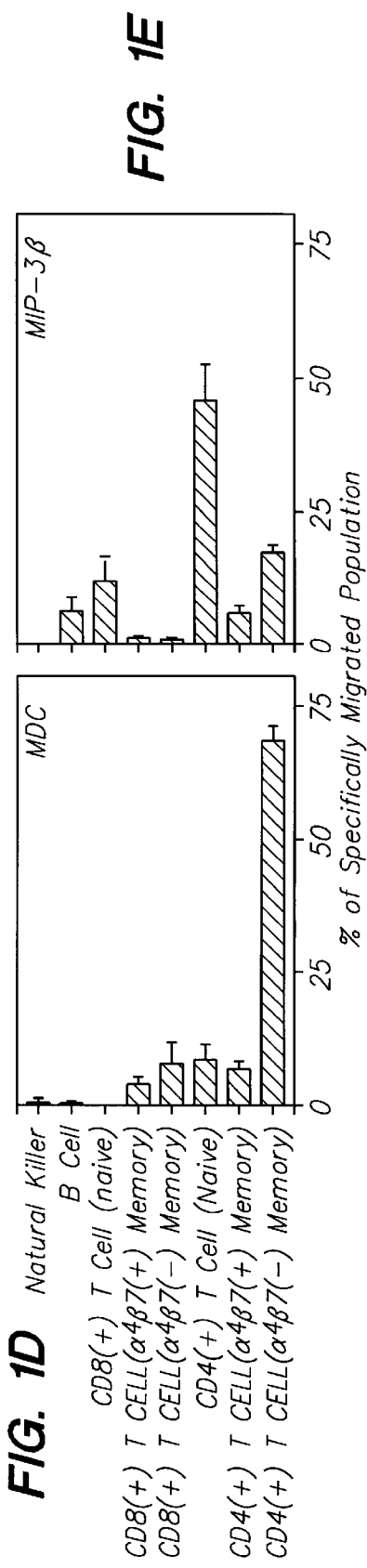

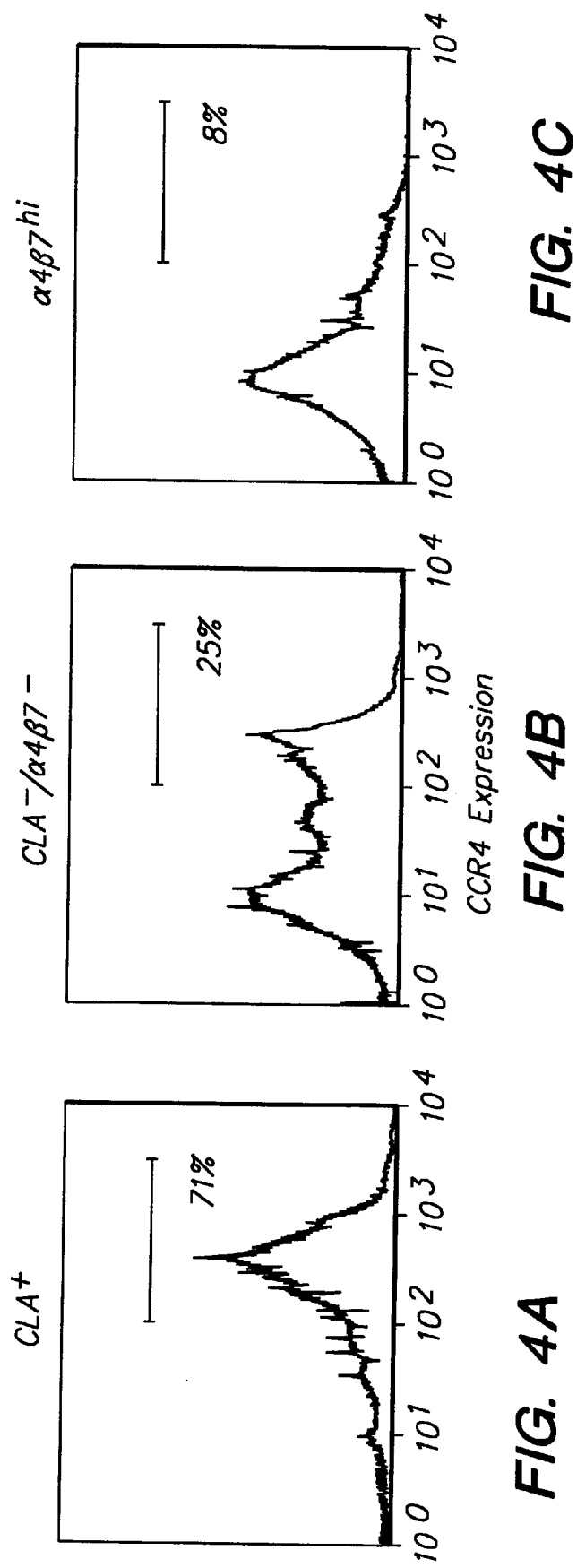

SEQUENCE LISTING

```
<160> NUMBER OF SEQ ID NOS: 6

<210> SEQ ID NO 1
<211> LENGTH: 1677
<212> TYPE: DNA
<213> ORGANISM: H. sapiens
<220> FEATURE:
<221> NAME/KEY: CDS
<222> LOCATION: (183)...(1265)
<223> OTHER INFORMATION: CCR4, Chemokine receptor coding sequence

<400> SEQUENCE: 1
cgggggtttt gatcttcttc ccttcttt cttccctttc ttctttcctt cctccctccc      60
tctctcattt cccttctcct tctccctcag tctccacatt caacattgac aagtccattc    120
```

```
agaaaagcaa gctgcttctg gttgggccca gacctgcctt gaggagcctg tagagttaaa        180 aa atg aac ccc acg gat ata gca gat acc acc ctc gat gaa agc ata          227
   Met Asn Pro Thr Asp Ile Ala Asp Thr Thr Leu Asp Glu Ser Ile
    1               5                  10                  15 tac agc aat tac tat ctg tat gaa agt atc ccc aag cct tgc acc aaa         275
Tyr Ser Asn Tyr Tyr Leu Tyr Glu Ser Ile Pro Lys Pro Cys Thr Lys
                20                  25                  30 gaa ggc atc aag gca ttt ggg gag ctc ttc ctg ccc cca ctg tat tcc         323
Glu Gly Ile Lys Ala Phe Gly Glu Leu Phe Leu Pro Pro Leu Tyr Ser
                35                  40                  45 ttg gtt ttt gta ttt ggt ctg ctt gga aat tct gtg gtg gtt ctg gtc         371
Leu Val Phe Val Phe Gly Leu Leu Gly Asn Ser Val Val Val Leu Val
            50                  55                  60 ctg ttc aaa tac aag cgg ctc agg tcc atg act gat gtg tac ctg ctc         419
Leu Phe Lys Tyr Lys Arg Leu Arg Ser Met Thr Asp Val Tyr Leu Leu
        65                  70                  75 aac ctt gcc atc tcg gat ctg ctc ttc gtg ttt tcc ctc cct ttt tgg         467
Asn Leu Ala Ile Ser Asp Leu Leu Phe Val Phe Ser Leu Pro Phe Trp
 80                  85                  90                  95 ggc tac tat gca gca gac cag tgg gtt ttt ggg cta ggt ctg tgc aag         515
Gly Tyr Tyr Ala Ala Asp Gln Trp Val Phe Gly Leu Gly Leu Cys Lys
                100                 105                 110 atg att tcc tgg atg tac ttg gtg ggc ttt tac agt ggc ata ttc ttt         563
Met Ile Ser Trp Met Tyr Leu Val Gly Phe Tyr Ser Gly Ile Phe Phe
            115                 120                 125 gtc atg ctc atg agc att gat aga tac ctg gcg ata gtg cac gcg gtg         611
Val Met Leu Met Ser Ile Asp Arg Tyr Leu Ala Ile Val His Ala Val
        130                 135                 140 ttt tcc ttg agg gca agg acc ttg act tat ggg gtc atc acc agt ttg         659
Phe Ser Leu Arg Ala Arg Thr Leu Thr Tyr Gly Val Ile Thr Ser Leu
    145                 150                 155 gct aca tgg tca gtg gct gtg ttc gcc tcc ctt cct ggc ttt ctg ttc         707
Ala Thr Trp Ser Val Ala Val Phe Ala Ser Leu Pro Gly Phe Leu Phe
160                 165                 170                 175 agc act tgt tat act gag cgc aac cat acc tac tgc aaa acc aag tac         755
Ser Thr Cys Tyr Thr Glu Arg Asn His Thr Tyr Cys Lys Thr Lys Tyr
                180                 185                 190 tct ctc aac tcc acg acg tgg aag gtt ctc agc tcc ctg gaa atc aac         803
Ser Leu Asn Ser Thr Thr Trp Lys Val Leu Ser Ser Leu Glu Ile Asn
            195                 200                 205 att ctc gga ttg gtg atc ccc tta ggg atc atg ctg ttt tgc tac tcc         851
Ile Leu Gly Leu Val Ile Pro Leu Gly Ile Met Leu Phe Cys Tyr Ser
        210                 215                 220 atg atc atc agg acc ttg cag cat tgt aaa aat gag aag aag aac aag         899
Met Ile Ile Arg Thr Leu Gln His Cys Lys Asn Glu Lys Lys Asn Lys
    225                 230                 235 gcg gtg aag atg atc ttt gcc gtg gtg gtc ctc ttc ctt ggg ttc tgg         947
Ala Val Lys Met Ile Phe Ala Val Val Val Leu Phe Leu Gly Phe Trp
240                 245                 250                 255 aca cct tac aac ata gtg ctc ttc cta gag acc ctg gtg gag cta gaa         995
Thr Pro Tyr Asn Ile Val Leu Phe Leu Glu Thr Leu Val Glu Leu Glu
                260                 265                 270 gtc ctt cag gac tgc acc ttt gaa aga tac ttg gac tat gcc atc cag        1043
Val Leu Gln Asp Cys Thr Phe Glu Arg Tyr Leu Asp Tyr Ala Ile Gln
            275                 280                 285 gcc aca gaa act ctg gct ttt gtt cac tgc tgc ctt aat ccc atc atc        1091
Ala Thr Glu Thr Leu Ala Phe Val His Cys Cys Leu Asn Pro Ile Ile
        290                 295                 300 tac ttt ttt ctg ggg gag aaa ttt cgc aag tac atc cta cag ctc ttc        1139
```

```
                Tyr Phe Phe Leu Gly Glu Lys Phe Arg Lys Tyr Ile Leu Gln Leu Phe
                    305                 310                 315 aaa acc tgc agg ggc ctt ttt gtg ctc tgc caa tac tgt ggg ctc ctc       1187
Lys Thr Cys Arg Gly Leu Phe Val Leu Cys Gln Tyr Cys Gly Leu Leu
320                 325                 330                 335 caa att tac tct gct gac acc ccc agc tca tct tac acg cag tcc acc       1235
Gln Ile Tyr Ser Ala Asp Thr Pro Ser Ser Tyr Thr Gln Ser Thr
                    340                 345                 350 atg gat cat gat ctt cat gat gct ctg tag gaaaaatgaa atggtgaaat         1285
Met Asp His Asp Leu His Asp Ala Leu
                    355                 360 gcagagtcaa tgaactttc cacattcaga gcttacttta aaattggtat ttttaggtaa      1345
gagatccctg agccagtgtc aggaggaagg cttacaccca cagtggaaag acagcttctc     1405
atcctgcagg cagcttttc tctcccacta gacaagtcca gcctggcaag ggttcacctg      1465
ggctgaggca tccttcctca caccaggctt gcctgcaggc atgagtcagt ctgatgagaa     1525
ctctgagcag tgcttgaatg aagttgtagg taatattgca aggcaaagac tattcccttc     1585
taacctgaac tgatgggttt ctccagaggg aattgcagag tactggctga tggagtaaat     1645
cgctaccttt tgctgtggca aatgggcccc cg                                   1677

<210> SEQ ID NO 2
<211> LENGTH: 360
<212> TYPE: PRT
<213> ORGANISM: H. sapiens

<400> SEQUENCE: 2

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
                20                  25                  30

Gly Ile Lys Ala Phe Gly Glu Leu Phe Leu Pro Pro Leu Tyr Ser Leu
            35                  40                  45

Val Phe Val Phe Gly Leu Leu Gly Asn Ser Val Val Val Leu Val Leu
        50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
                100                 105                 110

Ile Ser Trp Met Tyr Leu Val Gly Phe Tyr Ser Gly Ile Phe Phe Val
            115                 120                 125

Met Leu Met Ser Ile Asp Arg Tyr Leu Ala Ile Val His Ala Val Phe
        130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
                180                 185                 190

Leu Asn Ser Thr Thr Trp Lys Val Leu Ser Ser Leu Glu Ile Asn Ile
            195                 200                 205

Leu Gly Leu Val Ile Pro Leu Gly Ile Met Leu Phe Cys Tyr Ser Met
        210                 215                 220
```

```
Ile Ile Arg Thr Leu Gln His Cys Lys Asn Glu Lys Asn Lys Ala
225                 230                 235                 240

Val Lys Met Ile Phe Ala Val Val Leu Phe Leu Gly Phe Trp Thr
                245                 250                 255

Pro Tyr Asn Ile Val Leu Phe Leu Glu Thr Leu Val Glu Leu Glu Val
                260                 265                 270

Leu Gln Asp Cys Thr Phe Glu Arg Tyr Leu Asp Tyr Ala Ile Gln Ala
                275                 280                 285

Thr Glu Thr Leu Ala Phe Val His Cys Cys Leu Asn Pro Ile Ile Tyr
        290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
                340                 345                 350

Asp His Asp Leu His Asp Ala Leu
                355                 360

<210> SEQ ID NO 3
<211> LENGTH: 538
<212> TYPE: DNA
<213> ORGANISM: H. sapiens
<220> FEATURE:
<221> NAME/KEY: CDS
<222> LOCATION: (53)...(337)
<223> OTHER INFORMATION: Coding sequence for TARC chemokine

<400> SEQUENCE: 3
ccctgagcag agggacctgc acacagagac tccctcctgg gctcctggca cc atg gcc    58
                                                          Met Ala
                                                           1 cca ctg aag atg ctg gcc ctg gtc acc ctc ctc ctg ggg gct tct ctg    106
Pro Leu Lys Met Leu Ala Leu Val Thr Leu Leu Leu Gly Ala Ser Leu
      5                  10                  15 cag cac atc cac gca gct cga ggg acc aat gtg ggc cgg gag tgc tgc    154
Gln His Ile His Ala Ala Arg Gly Thr Asn Val Gly Arg Glu Cys Cys
 20                  25                  30 ctg gag tac ttc aag gga gcc att ccc ctt aga aag ctg aag acg tgg    202
Leu Glu Tyr Phe Lys Gly Ala Ile Pro Leu Arg Lys Leu Lys Thr Trp
 35                  40                  45                  50 tac cag aca tct gag gac tgc tcc agg gat gcc atc gtt ttt gta act    250
Tyr Gln Thr Ser Glu Asp Cys Ser Arg Asp Ala Ile Val Phe Val Thr
              55                  60                  65 gtg cag ggc agg gcc atc tgt tcg gac ccc aac aac aag aga gtg aag    298
Val Gln Gly Arg Ala Ile Cys Ser Asp Pro Asn Asn Lys Arg Val Lys
          70                  75                  80 aat gca gtt aaa tac ctg caa agc ctt gag agg tct tga agcctcctca    347
Asn Ala Val Lys Tyr Leu Gln Ser Leu Glu Arg Ser
          85                  90 ccccagactc ctgactgtct cccgggacta cctgggacct ccaccgttgg tgttcaccgc    407
ccccaccctg agcgcctggg tccaggggag gccttccagg gacgaagaag agccacagtg    467
agggagatcc catccccttg tctgaactgg agccatgggc acaaagggcc cagattaaag    527
tctttatcct c                                                         538

<210> SEQ ID NO 4
<211> LENGTH: 94
<212> TYPE: PRT
```

-continued

```
<213> ORGANISM: H. sapiens

<400> SEQUENCE: 4

Met Ala Pro Leu Lys Met Leu Ala Leu Val Thr Leu Leu Gly Ala
 1               5                  10                  15

Ser Leu Gln His Ile His Ala Ala Arg Gly Thr Asn Val Gly Arg Glu
                20                  25                  30

Cys Cys Leu Glu Tyr Phe Lys Gly Ala Ile Pro Leu Arg Lys Leu Lys
            35                  40                  45

Thr Trp Tyr Gln Thr Ser Glu Asp Cys Ser Arg Asp Ala Ile Val Phe
    50                  55                  60

Val Thr Val Gln Gly Arg Ala Ile Cys Ser Asp Pro Asn Asn Lys Arg
65                  70                  75                  80

Val Lys Asn Ala Val Lys Tyr Leu Gln Ser Leu Glu Arg Ser
                85                  90

<210> SEQ ID NO 5
<211> LENGTH: 2923
<212> TYPE: DNA
<213> ORGANISM: H. sapiens
<220> FEATURE:
<221> NAME/KEY: CDS
<222> LOCATION: (20)...(301)
<223> OTHER INFORMATION: Coding sequence for MDC chemokine

<400> SEQUENCE: 5
gagacataca ggacagagc atg gct cgc cta cag act gca ctc ctg gtt gtc        52
                    Met Ala Arg Leu Gln Thr Ala Leu Leu Val Val
                     1               5                  10 ctc gtc ctc ctt gct gtg gcg ctt caa gca act gag gca ggc ccc tac        100
Leu Val Leu Leu Ala Val Ala Leu Gln Ala Thr Glu Ala Gly Pro Tyr
            15                  20                  25 ggc gcc aac atg gaa gac agc gtc tgc tgc cgt gat tac gtc cgt tac        148
Gly Ala Asn Met Glu Asp Ser Val Cys Cys Arg Asp Tyr Val Arg Tyr
        30                  35                  40 cgt ctg ccc ctg cgc gtg gtg aaa cac ttc tac tgg acc tca gac tcc        196
Arg Leu Pro Leu Arg Val Val Lys His Phe Tyr Trp Thr Ser Asp Ser
    45                  50                  55 tgc ccg agg cct ggc gtg gtg ttg cta acc ttc agg gat aag gag atc        244
Cys Pro Arg Pro Gly Val Val Leu Leu Thr Phe Arg Asp Lys Glu Ile
60                  65                  70                  75 tgt gcc gat ccc aga gtg ccc tgg gtg aag atg att ctc aat aag ctg        292
Cys Ala Asp Pro Arg Val Pro Trp Val Lys Met Ile Leu Asn Lys Leu
                80                  85                  90 agc caa tga agagcctact ctgatgaccg tggccttggc tcctccagga               341
Ser Gln aggctcagga gccctacctc cctgccatta tagctgctcc ccgccagaag cctgtgccaa        401
ctctctgcat tccctgatct ccatcccgt ggctgtcacc cttggtcacc tccgtgctgt         461
cactgccatc tccccctga cccctctaac ccatcctctg cctccctccc tgcagtcaga         521
gggtcctgtt cccatcagcg attcccctgc ttaaaccctt ccatgactcc ccactgccct         581
aagctgaggt cagtctccca agcctggcat gtggccctct ggatctgggt tccatctctg         641
tctccagcct gccacttcc cttcatgaat gttgggttct agctccctgt tctccaaacc         701
catactacac atcccacttc tgggtctttg cctgggatgt tgctgacact cagaaagtcc         761
caccacctgc acatgtgtag ccccaccagc cctccaaggc attgctcgcc caagcagctg         821
gtaattccat ttcatgtatt agatgtcccc tggccctctg tccctctta ataaccctag         881
```

-continued

```
tcacagtctc cgcagattct tgggatttgg gggttttctc ccccacctct ccactagttg    941
gaccaaggtt tctagctaag ttactctagt ctccaagcct ctagcataga gcactgcaga   1001
caggccctgg ctcagaatca gagcccagaa agtggctgca gacaaaatca ataaaactaa   1061
tgtccctccc ctctccctgc caaaaggcag ttacatatca atacagagac tcaaggtcac   1121
tagaaatggg ccagctggt caatgtgaag ccccaaattt gcccagattc acctttcttc   1181
ccccactccc tttttttttt tttttttttt gagatggagt ttcgctcttg tcacccacgc   1241
tggagtgcaa tggtgtggtc ttggcttatt gaagcctctg cctcctgggt tcaagtgatt   1301
ctcttgcctc agcctcctga gtagctggga ttacaggttc ctgctaccac gcccagctaa   1361 ttttttgtatt tttagtagag acgaggcttc accatgttgg ccaggctggt ctcgaactcc   1421
tgtcctcagg taatccgccc acctcagcct cccaaagtgc tgggattaca ggcgtgagcc   1481
acagtgcctg gcctcttccc tctccccact gcccccccca actttttttt tttttttatg   1541
gcagggtctc actctgtcgc ccaggctgga gtgcagtggc gtgatctcgg ctcactacaa   1601
cctcgacctc ctgggttcaa gtgattctcc caccccagcc tcccaagtag ctgggattac   1661
aggtgtgtgc cactacggct ggctaatttt tgtattttta gtagagacag gtttcaccat   1721
attggccagg ctggtcttga actcctgacc tcaagtgatc caccttcctt gtgctcccaa   1781
agtgctgaga ttacaggcgt gagctatcac acccagcctc ccctttttt tcctaatagg   1841 agactcctgt accttttcttc gttttaccta tgtgtcgtgt ctgcttacat ttccttctcc   1901
cctcaggctt tttttgggtg gtcctccaac ctccaatacc caggcctggc ctcttcagag   1961 tacccccat tccactttcc ctgcctcctt ccttaaatag ctgacaatca aattcatgct   2021
atggtgtgaa agactacctt tgacttggta ttataagctg gagttatata tgtatttgaa   2081
aacagagtaa atacttaaga ggccaaatag atgaatggaa gaattttagg aactgtgaga   2141
gggggacaag gtgaagcttt cctggccctg ggaggaagct ggctgtggta gcgtagcgct   2201
ctctctctct gtctgtggca ggagccaaag agtagggtgt aattgagtga aggaatcctg   2261
ggtagagacc attctcaggt ggttgggcca ggctaaagac tgggagttgg gtctatctat   2321
gcctttctgg ctgattttg tagagacggg gttttgccat gttacccagg ctggtctcaa   2381
actcctgggc tcaagcgatc ctcctggctc agcctcccaa agtgctggga ttacaggcgt   2441
gaatcactgc gcctggcttc ctcttcctct tgagaaatat tcttttcata cagcaagtat   2501
gggacagcag tgtcccaggt aaaggacata atgttacaa gtgtctggtc ctttctgagg   2561
gaggctggtg ccgctctgca gggtatttga acctgtggaa ttggaggagg ccatttcact   2621
ccctgaaccc agcctgacaa atcacagtga gaatgttcac cttataggct tgctgtgggg   2681
ctcaggttga aagtgtgggg agtgacactg cctaggcatc cagctcagtg tcatccaggg   2741
cctgtgtccc tcccgaaccc agggtcaacc tgcctgccac aggcactaga aggacgaatc   2801
tgcctactgc ccatgaacgg ggccctcaag cgtcctggga tctccttctc cctcctgtcc   2861
tgtccttgcc cctcaggact gctggaaaat aaatcctta aaatagtaaa aaaaaaaaa    2921 aa                                                                  2923
```

<210> SEQ ID NO 6
<211> LENGTH: 93
<212> TYPE: PRT
<213> ORGANISM: H. sapiens

<400> SEQUENCE: 6

Met Ala Arg Leu Gln Thr Ala Leu Leu Val Val Leu Val Leu Leu Ala

-continued

```
1               5               10              15
Val Ala Leu Gln Ala Thr Glu Ala Gly Pro Tyr Gly Ala Asn Met Glu
            20              25              30

Asp Ser Val Cys Cys Arg Asp Tyr Val Arg Tyr Arg Leu Pro Leu Arg
        35              40              45

Val Val Lys His Phe Tyr Trp Thr Ser Asp Ser Cys Pro Arg Pro Gly
    50              55              60

Val Val Leu Leu Thr Phe Arg Asp Lys Glu Ile Cys Ala Asp Pro Arg
65              70              75              80

Val Pro Trp Val Lys Met Ile Leu Asn Lys Leu Ser Gln
            85              90
```

MODULATION OF SYSTEMIC MEMORY T CELL TRAFFICKING

GOVERNMENT SUPPORT

This work is supported at least in part by grants from the N.I.H. GM37734; and NIH Individual National Research Service Award 1F32AI08930, and was carried out in part in facilities of the Department of Veterans Affairs. The government may have certain rights in this invention.

INTRODUCTION

BACKGROUND

During inflammation and immune responses, leukocytes leave the blood and accumulate at the site of insult. A family of cytokines called chemokines recruit subsets of leukocytes, and are also involved in acute and chronic inflammatory processes as well as hematopoiesis. Chemokines are a subclass of cytokines, which have distinct structural features and biological effects. Their primary activity is on the chemotaxis of leukocytes, but they are also reported to have angiogenic and angiostatic effects. All chemokines bind to members of a G-protein coupled serpentine receptor superfamily that span the leukocyte cell surface membrane seven times (7-TM). The alpha or CXC chemokines are characterized by a single amino acid separating the first 2 cysteines. The beta or CC family of chemokines contain 2 adjacent cysteines. The human genes for the CC chemokines are clustered on chromosome 17q11-q12.

Chemokines are critical in the migration of leukocytes from the circulatory system to tissues, for example during inflammation processes. Most chemokines possess two major binding surfaces: a high affinity site responsible for specific ligand/receptor interactions and a lower affinity site, also called the heparin-binding or glycosaminoglycan-binding domain, believed to be responsible for the establishment and presentation of chemokine gradients on the surface of endothelial cells and within the extracellular matrix. Leukocytes are able to bind to the chemokine gradient through the high affinity receptor, which then induces remodeling of the leukocyte cytoskeleton, allowing flattening and cellular polarization. Once outside the circulation, chemokines also guide leukocytes to target tissues.

The chemokine receptor CCR4 was first identified by Power et al. (1995) *J. Biol. Chem.* 270:19495–19500 (Genbank accession number X85740). It was originally reported that the CC chemokines MIP-1, MCP-1 and RANTES were able to functionally interact with CCR4. However, recent data has suggested that this receptor is specific for the chemokines TARC and MDC. CCR4 mRNA is present in basophils, T cells, and monocytes, which is consistent with the finding that chemokines have been previously shown to exert a diverse range of activities on these cell types, including histamine release, chemotaxis, and $Ca^{++}$ mobilization in basophils, and chemotaxis in T cells and monocytes. The expression of CCR4 on Th2 cells has been reported to be transiently increased following TCR and CD28 engagement (D'Ambrosio et al. (1998) *J Immunol* 161:5111–5). Activated Th1 cells also up-regulate CCR4 expression and functional responsiveness to thymus- and activation-regulated chemokine. Analysis of polarized subsets of CD8+ T cells reveals a similar pattern of chemokine receptor expression and modulation of responsiveness.

The chemokine TARC (thymus and activation-regulated chemokine) was first cloned by lmai et al. (1996) *J. Biol. Chem.* 271:21514–21521. TARC is expressed transiently in phytohemagglutinin-stimulated peripheral blood mononuclear cells and constitutively in thymus. Radiolabeled recombinant TARC bound specifically to T-cell lines and peripheral T cells but not to monocytes or granulocytes, and is able to elicit a chemotactic response. Expression of TARC may be upregulated by cytokines known to be produced by TH2 type T cells.

Macrophage-derived chemokine (MDC) is a recently identified member of the CC chemokine family. MDC is not closely related to other chemokines, sharing most similarity with TARC. Northern blot analysis indicates high expression of MDC in macrophages and in monocyte-derived dendritic cells, but not in monocytes, natural killer cells, or several cell lines of epithelial, endothelial, or fibroblast origin. There are also high expression levels in thymus and lower expression in lung and spleen.

Both MDC and TARC function as chemoattractants for CCR4 transfectants. Since MDC and TARC are both expressed in the thymus, it has been suggested that a role for these chemokines may be to attract CCR4-bearing thymocytes in the process of T cell education and differentiation (Imai et al. (1998) *J Biol Chem* 273(3):1764–1768).

Although chemokines are clearly beneficial in wound healing, hematopoiesis, and the clearance of infectious organisms, the continued expression of chemokines is associated with chronic inflammation. Therefore, this class of cytokines and/or their receptors are an attractive target for the creation of antagonists that abrogate one or more chemokine functions. It is envisioned that such antagonists could serve as a new class of anti-inflammatory drugs.

Relevant Literature

The role of chemokines in leukocyte trafficking is reviewed by Baggiolini (1998) *Nature* 392:565–8, in which it is suggested that migration responses in the complicated trafficking of lymphocytes of different types and degrees of activation will be mediated by chemokines. The use of small molecules to block chemokines is reviewed by Baggiolini and Moser (1997) J. Exp. Med. 186:1189–1191.

The role of various specific chemokines in lymphocyte homing has been previously described. For example, Campbell et al. (1998) Science, showed that SDF-1 (also called PBSF), 6-C-kine (also called Exodus-2), and MIP-3beta (also called ELC or Exodus-3) induced adhesion of most circulating lymphocytes, including most CD4+ T cells; and MIP-3alpha (also called LARC or Exodus-1) triggered adhesion of memory, but not naive, CD4+ T cells. Tangemann et al. (1998) *J. Immunol.* 161:6330–7 disclose the role of secondary lymphoid-tissue chemokine (SLC), a high endothelial venule (HEV)-associated chemokine, with the homing of lymphocytes to secondary lymphoid organs. Campbell et al. (1998) *J. Cell Biol* 141(4):1053–9 describe the receptor for SLC as CCR7, and that its ligand, SLC, can trigger rapid integrin-dependent arrest of lymphocytes rolling under physiological shear.

The expression of cutaneous lymphocyte antigen (CLA) in human CD4+ memory T cell differentiation, and its independent regulation with respect to cytokine synthesis, is discussed in Teraki and Picker (1997) *J Immunol* 159(12): 6018–29. The skin supports both Th1- and Th2-predominant responses in different settings; and the skin-homing capability of human memory T cells correlates with and appears to depend on expression of the skin-selective homing receptor CLA. The identification of CLA as a specialized form of P-selectin glycoprotein ligand-1 is disclosed in Fuhlbrigge et al. (1997) *Nature* 389(6654):978–81. CLA comprises a carbohydrate epitope that facilitates the targeting of T cells to inflamed skin, and is defined by both its reactivity with a unique monoclonal antibody, HECA-452, and its activity as a ligand for E-selectin (reviewed by Butcher and Picker (1996)).

A review of the biology of memory T cells may be found in Dutton et al. (1998) *Annu Rev Immunol* 16:201–23. Memory cells express a different pattern of cell surface markers, and they respond in several ways that are functionally different from those of naive cells. Human memory cells are CD45RA$^-$, CD45RO$^+$. In contrast to naive cells, memory cells secrete a full range of T cell cytokines.

SUMMARY OF THE INVENTION

Methods are provided to specifically modulate the trafficking of systemic memory T cells, particularly skin-homing cells expressing cutaneous lymphocyte antigen, CLA. Naive T cells and intestinal memory T cells are not affected by the subject methods. Systemic memory T cells express high levels of the chemokine receptor CCR4, and in response to CCR4 agonists these cells undergo integrin-dependent arrest. In one embodiment of the invention, naturally occurring CCR4 ligands, which include the chemokines TARC (thymus and activation-regulated chemokine) and MDC (macrophage derived chemokine), are used to specifically attract systemic memory T cells. Alternative agonists for use as attractants include antibodies and other compounds having specific binding moieties to CCR4. In another embodiment of the invention, the trafficking of memory T cells is prevented by the administration of CCR4 blocking agents; compounds that otherwise prevent the binding of natural CCR4 ligands to CCR4; or compounds that prevent expression of, or signaling through, CCR4.

BRIEF DESCRIPTION OF THE DRAWINGS

FIGS. 1A to 1E show that skin-homing memory T cells are preferentially attracted by TARC and MDC. A comparison is made of unfractionated lymphocytes from peripheral blood (FIG. 1A) with lymphocytes specifically attracted to various chemokines (FIG. 1B to FIG. 1E).

FIG. 4 shows differential CCR4 expression in CD4(+) memory T cell subsets defined by homing receptor expression.

DESCRIPTION OF THE SPECIFIC EMBODIMENTS

Figure 2:
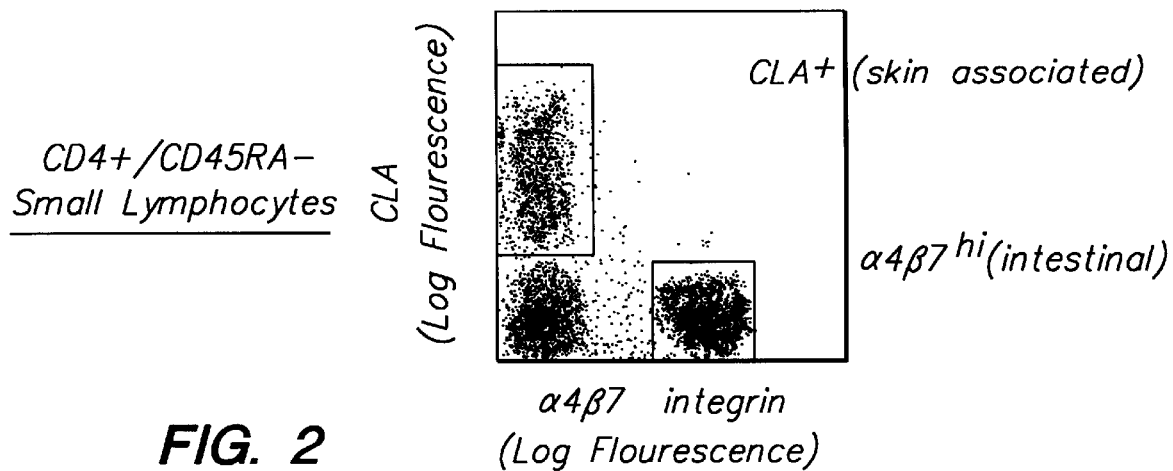
FIG. 2 shows the flow cytometry gates used to calculate percent migration in FIG. 3.

Methods are provided to specifically modulate the trafficking of systemic memory T cells, particularly CD4$^+$ T cells, without affecting naive T cells and intestinal memory T cells. Systemic memory T cells express high levels of the chemokine receptor CCR4, and in response to CCR4 agonists these cells are triggered to undergo integrin-dependent arrest at a target site. This arrest acts to localize the cells at the target site. In some embodiments of the invention, this trigger is manipulated to modulate the adhesion of these T cells to endothelial cells. The methods of the invention may also modulate the chemotaxis of these T cells, which may also control their trafficking and interactions in systemic sites of inflammation.

In the subject methods, compounds that modulate the triggering activity of CCR4 are administered systemically or locally to alter the trafficking behavior of the memory T cells. Trafficking, or homing, is used herein to refer to the biological activities and pathways that control the localization of leukocytes in a mammalian host. Such trafficking may be associated with disease, e.g. inflammation, allergic reactions, etc., or may be part of normal biological homeostasis.

Local administration that provides for a prolonged localized concentration, which may utilize sustained release implants or other topical formulation, is of particular interest. In one embodiment of the invention the trigger modulating compound is an agonist of CCR4, which acts to enhance the triggering effect. In an alternative embodiment, the trigger modulating compound blocks CCR4 activity. In vivo uses of the method are of interest for therapeutic and investigational purposes. In vitro uses are of interest for drug screening, determination of physiological pathways, and the like. The subject methods also provide for targeting cells from blood to skin and other systemic sites of inflammation by expressing CCR4 on the cells to be targeted.

An advantage of the present invention is the selectivity for systemic memory T cells. Naive T cells are not affected, and therefore much of the normal cellular immunity is maintained. Another advantage is the selection for systemic vs. intestinal memory T cells. There are many conditions that benefit from selective modulation of memory T cells. For example, many conditions of chronic inflammation and autoimmunity are mediated by memory T cells, and are improved by preventing such T cells from accumulating target sites by the administration of agents that block CCR4 triggering. Such treatment may be prophylactic, e.g. to prevent the onset of disease, or may be used to treat existing disease.

The data presented herein demonstrate that systemic memory T cells, which are characterized as CD45RA$^-$, and integrin α4β7$^-$, express high levels of CCR4. Ligands of CCR4 ligands, such as TARC or MDC, act as an adhesion trigger. Upon CCR4 binding, these cells undergo integrin-dependent arrest to the appropriate vascular receptor(s). Of particular interest are skin-homing memory T cells, which express high levels of CLA. The binding to CCR4 triggers arrest of these cells, mediated by the binding of CLA to its counter-receptor, E-selectin. Other systemic memory T cells undergo LFA-1-dependent lymphocyte adhesion to ICAM-1.

For convenience, the nucleic acid sequences (SEQ ID NOS:1, 3, 5) and amino acid sequences (SEQ ID NOS:2, 4, 6) of the native human CCR4, TARC and MDC molecules are provided herein. Unless otherwise specified, references to the molecules made herein are to the molecules corresponding to these sequences. Nucleic acids having these sequences may be used to produce the encoded polypeptides, e.g. to produce antigen for immunization, for binding studies, to transfect CCR4 into T cells to enhance trafficking, etc.

Systemic memory T cells are characterized according to the cell surface expression of certain known antigens. Typically these cells are positive for CD4, and lack expression of CD45RA, and integrin $\alpha 4\beta 7$. They are further characterized by expression of CCR4. A subset of cells of interest are CLA$^+$. Verification of the identity of the cells of interest may be performed by any convenient method, including antibody staining and analysis by fluorescence detection, ELISA, etc., reverse transcriptase PCR, transcriptional amplification and hybridization to nucleic acid microarrays, etc.

Some memory T cells associated with the skin are known to express CLA, and such cells are of particular interest for treatment with the present methods, particularly to modulate the trafficking, or homing of these cells to cutaneous tissues. Conditions of inflammation-associated or allergic reaction patterns of the skin include atopic dermatitis or infantile eczema; contact dermatitis, psoriasis, lichen planus; hypersensitivity or destructive responses to infectious agents, etc. Such diseases benefit from the administration of CCR4 agonists. The treatment decreases the number of systemic memory T cells at the sites of inflammation.

Other systemic memory cells are triggered to adhere to endothelial ICAM-1, by LFA-1 binding. These adhesion molecules are implicated directly in graft rejection, psoriasis, and arthritis. A CCR4 blocking agent that prevents triggering of LFA-1 mediated adhesion is useful in the inhibition of graft rejection by preventing the accumulation of memory T cells at the site of graft implantation; preventing intra-islet infiltration by T cells to inhibit development of insulin-dependent diabetes mellitus; blocking infiltration of T cells into the central nervous system to treat multiple sclerosis and other demyelinating diseases; blocking the accumulation of T cells in the synovial joints of patients suffering from rheumatoid arthritis; accumulation of memory T cells to influence immune responsiveness, and the like.

CCR4 agonists are useful in enhancing the immune reaction at a targeted site. For example, in burn patients it may be desirable to prophylactically increase the memory T cell population at the burn sites. Other infections, particularly localized infections, may be treated this way, including, without limitation, human herpes viruses including herpes simplex viruses (HSV) types 1 and 2, Epstein Barr virus (EBV), cytomegalovirus (CMV), varicella zoster virus (VZV) and human herpes virus 6 (HHV-6), particularly infections of the mouth and genitals, hepatitis B virus (HBV) and hepatitis C virus (HCC) infections of the liver, etc.

CCR4 modulating agents are molecules that specifically act as an agonist to enhance CCR4 biological activity; or that act as antagonists that block CCR4 biological activity, for example the interaction between CCR4 and its ligands. Often such agents interact with the extracellular binding domain or transmembrane domain of CCR4 protein, and may activate the molecule through the ligand binding site, block the ligand binding site, conformationally alter the receptor, etc. Usually the binding affinity of the blocking agent will be at least about 100 $\mu$M. Preferably the blocking agent will be substantially unreactive with related molecules to CCR4, such as CCR1, CCR2, CCR3, CCR5, etc. and other members of the seven transmembrane domain superfamily. Blocking agents do not activate CCR4 triggering of adhesion. Agonists may activate the triggering activity, enhance chemotaxis activity, or enhance the triggering activity of other ligands. It will be understood by one of skill in the art that the following discussions of cross-reactivity and competition between different molecules is intended to refer to molecules having the same species of origin, e.g. human CCR4 binds human TARC and MDC, etc.

Candidate modulating agents are screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified CCR4 protein, or alternatively may use native memory T cells that express CCR4, or other cells, e.g. cells transfected with an expression construct for CCR4; membranes from these cells; etc. As an example of a binding assay, purified CCR4 protein is bound to an insoluble support, e.g. microtiter plate, magnetic beads, etc. The candidate modulating agent and soluble, labeled TARC or MDC are added to the cells, and the unbound components are then washed off. The ability of the modulating agent to compete with TARC and MDC for CCR4 binding is determined by quantitation of bound, labeled TARC or MDC. Confirmation that the blocking agent does not cross-react with other chemokine receptors may be performed with a similar assay, substituting CCR1, CCR2, etc. for CCR4. Suitable molecules will have at least about $10^2$ less binding to other chemokine receptors than to CCR4, more usually at least about $10^3$ less binding.

A number of screening assays are available for blocking agents. The components of such assays will typically include CCR4 protein; and optionally a CCR4 activating agent, e.g. TARC, MDC, etc. The assay mixture will also comprise a candidate pharmacological agent. Generally a plurality of assay mixtures are run in parallel with different agent concentrations to obtain a differential response to the various concentrations. Typically, one of these concentrations serves as a negative control, i.e. at zero concentration or below the level of detection.

Conveniently, in these assays one or more of the molecules will be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures.

A variety of other reagents may be included in the screening assay. These include reagents like salts, neutral proteins, e.g. albumin, detergents, etc which may be used to facilitate optimal protein-DNA binding and/or reduce non-specific or background interactions. Also reagents that otherwise improve the efficiency of the assay, such as protease inhibitors, nuclease inhibitors, anti-microbial agents, etc. may be used.

A functional assay that detects T cell adhesion triggering may be used for confirmation. For example, a population of systemic memory T cells may be stimulated with TARC or MDC, in the presence or absence of the candidate modulating agent. An agent that blocks CCR4 triggering will cause a decrease in the T cell adhesion to the appropriate endothelial cell molecule, e.g. LFA-1 or E-selectin, as measured by the assays described in the examples provided herein, etc. An agent that is a CCR4 agonist will increase adhesion of the T cells to such an endothelial cell molecule, either in the absence, or in the presence of CCR4 ligands.

CCR4 modulating agents are peptides, small organic molecules, peptidomimetics, soluble T cell receptors, antibodies, or the like. Antibodies are an exemplary modulating agent. Antibodies may be polyclonal or monoclonal; intact or truncated, e.g. F(ab')$_2$, Fab, Fv; xenogeneic, allogeneic, syngeneic, or modified forms thereof, e.g. humanized, chimeric, etc.

In many cases, the modulating agent will be an oligopeptide, e.g. antibody or fragment thereof, etc., but other molecules that provide relatively high specificity and affinity may also be employed. Combinatorial libraries provide compounds other than oligopeptides that have the necessary binding characteristics. Generally, the affinity will be at least about $10^{-6}$, more usually about $10^{-8}$ M, i.e. binding affinities normally observed with specific monoclonal antibodies.

Candidate agents also encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl, sulfhydryl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Suitable antibodies for use as blocking agents are obtained by immunizing a host animal with peptides comprising all or a portion of CCR4 protein. Suitable host animals include mouse, rat sheep, goat, hamster, rabbit, etc. The origin of the protein immunogen may be mouse, human, rat, monkey etc. The host animal will generally be a different species than the immunogen, e.g. mouse CCR4 used to immunize hamsters, human CCR4 to immunize mice, etc.

The immunogen may comprise the complete protein, or fragments and derivatives thereof. Preferred immunogens comprise all or a part of the extracellular domain of human CCR4, where these residues contain post-translation modifications, such as glycosylation, found on the native protein. Immunogens comprising the extracellular domain are produced in a variety of ways known in the art, e.g. expression of cloned genes using conventional recombinant methods, isolation from T cells, sorted cell populations expressing high levels of CCR4, etc. Where expression of a recombinant or modified protein is desired, a vector encoding the desired portion of CCR4 will be used. Generally, an expression vector will be designed so that the extracellular domain of the CCR4 molecule is on the surface of a transfected cell, or alternatively, the extracellular domain is secreted from the cell.

Monoclonal antibodies are produced by conventional-techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using CCR4 bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the blocking agent. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91–3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

The formulation of CCR4 modulating agent is administered at a dose effective to alter the accumulation of systemic memory T cells at the targeted site, e.g. a site of inflammation, cutaneous tissue, etc. The subject invention is useful in any species, such as primate, particularly human, domestic animals, e.g. murine, bovine, equine, canine, feline, ovine, porcine, etc., and any of these species may find application as a source of antibodies.

The antibodies or other binding molecules used in the method of the present invention are preferably administered to individuals in a manner that will maximize the likelihood of the antibody or other epitope-binding molecule reaching the targeted cell, binding to it, and thereby modulating the interaction of chemokine and receptor. The dose for individuals of different species and for different diseases is determined by measuring the effect of the modulating agent on the lessening of parameters that are indicative of the disease being treated.

The CCR4 modulating agent can be given by various conventional administration routes, e.g. oral, rectal, intravenous, subcutaneous, intraperitoneal, transdermal, etc. Formulations of the CCR4 modulating agent are administered to a host affected by an immune disorder characterized by undesirable numbers of systemic memory T cells at a target site. The blocking agents of the invention are administered at a dosage that reduces the number of systemic memory T cells at a target site. The blocking agents of the present invention are administered at a dosage that reduces the numbers of memory T cells, thereby reducing T cell mediated immune activation, particularly chronic inflammation, while minimizing any side-effects. The CCR4 agonists enhance immune reactivity, for example as prophylaxis during trauma to the skin, e.g. burn victims and the like; as a treatment for infection; etc. It is contemplated that the composition will be obtained and used under the guidance of a physician for in vivo use.

Various methods for administration may be employed. The formulation may be given orally, by inhalation, or may be injected, e.g. intravascular, subcutaneous, intraperitoneal, intramuscular, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level.

The CCR4 modulating agents of the invention can be incorporated into a variety of formulations for therapeutic administration. More particularly, the agents can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the CCR4 modulating agents can be achieved in various ways, including oral, buccal, rectal, parenteral, intraperitoneal, intradermal, transdermal, intracheal, etc., administration. The agents may be systemic after administration or, preferably, are localized by the use of an implant that acts to retain the active dose at the site of implantation.

In pharmaceutical dosage forms, the CCR4 modulating agents may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the CCR4 modulating agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The CCR4 modulating agents complexes can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The CCR4 modulating agents complexes can be utilized in aerosol formulation to be administered via inhalation. The compounds of the present invention can be formulated into pressurized acceptable propellants such as dichlorodifluoromethane, propane, nitrogen and the like.

Furthermore, the CCR4 modulating agents complexes can be made into suppositories by mixing with a variety of bases such as emulsifying bases or water-soluble bases. The CCR4 modulating agents of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing CCR4 modulating agents is placed in proximity to the site of action, so that the local concentration of active agent is increased relative to the rest of the body.

The term "unit dosage form," as used herein, refers to physically discrete units suitable as unitary dosages for human and animal subjects, each unit containing a predetermined quantity of CCR4 modulating agents of the present invention calculated in an amount sufficient to produce the desired effect in association with a pharmaceutically acceptable diluent, carrier or vehicle. The specifications for the novel unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The compositions of the invention may also contain other therapeutically active agents. Of particular interest are combinations with other agents capable of additive or synergistic effect in achieving a therapeutic result, e.g. where a different or complementary pathway is affected by each of the active agents. The combined use of CCR4 modulating agent and other agents has the advantage that the required dosages for the individual drugs may be lower, and the onset and duration of effect of the different drugs complementary. In the combined therapy the different active agents may be delivered together or separately, and simultaneously or at different times within the day.

Those of skill will readily appreciate that dose levels can vary as a function of the specific compound, the severity of the symptoms and the susceptibility of the subject to side effects. Some of the specific complexes are more potent than others. Preferred dosages for a given agent are readily determinable by those of skill in the art by a variety of means. A preferred means is to measure the physiological potency of a given compound.

EXPERIMENTAL

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which scope will be determined by the language in the claims.

It must be noted that as used herein and in the appended claims, the singular forms "a", "and", and "the" include plural referents unless the context clearly dictates otherwise. Thus, for example, reference to "a mouse" includes a plurality of such mice and reference to "the cytokine" includes reference to one or more cytokines and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications mentioned herein are incorporated herein by reference for all relevant purposes, e.g., the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

EXAMPLE 1

To identify circulating lymphocyte subsets responsive to the CCR4 ligands, the phenotype of peripheral blood lymphocytes (PBL) migrating to its chemokine ligands TARC and MDC were analyzed in a standard transwell chemotaxis assay (Campbell et al. (1996) *J. Cell Biol.* 134, 255–266; Campbell et al. (1998) *J. Cell Biol.* 141, 1053–1059). Flow cytometric analyses were carried out to identify natural killer ($CD56^+$, $CD16^+$, $CD3^-$) cells, B cells ($CD19^+$), and naive ($CD45RA^+$) and memory ($CD45RA^-$) $CD4^+$ and $CD8^+$ T cells. Because of interest in determining the role of chemokines in regional lymphocyte trafficking, memory T cell sub-populations were also analyzed, as defined by expression of the integrin $\alpha 4\beta 7$, which is the lymphocyte receptor for the mucosal addressin cell adhesion molecule (MAdCAM-1). $\alpha 4\beta 7^{hi}$ memory lymphocytes bind to vascular MAdCAM-1, traffic to intestinal sites, and carry memory for intestinal antigens; whereas $\alpha 4\beta 7^-$ cells embody memory for systemic immune responses (Santamaria-Babi et al. (1995) *J. Exp. Med.* 181, 1935–1940). As illustrated in FIG. 1, all lymphocyte subsets except natural killer cells responded well to MIP3β (a ligand for CCR7), and all subsets migrated to SDF-1 (a ligand for CXCR4). In contrast, $\alpha 4\beta 7^-$ (non-intestinal, systemic) memory $CD4^+$ T cells were the predominant population recruited by TARC and by MDC; and $\alpha 4\beta 7^-$ memory phenotype $CD8^+$ cells were also enriched among lymphocytes responding to these chemokines.

Migration of human peripheral blood lymphocytes through 5 μm pores and FACs analysis of migrated cells was performed as described (Campbell et al. (1998), supra.) Lymphocyte subsets were defined as follows: Natural Killer=CD56(+), CD16(+), CD3(−); B Cell=CD19(+); CD8

(+) T Cell (naive)=TCRαβ(+), CD8(hi), CD27(+), CD45RA (hi); CD8(+) T Cell (α4β7(+) Memory)=CD8(hi), CD56(−), CD45RA(neg), α4β7(+); CD8(+) T Cell (α4β7(−) Memory)=CD8(hi), CD56(−), CD45RA(neg), α4β7(−); CD4(+) T Cell (naive)=CD4(+), CD45RA(+); CD4(+) T Cell (α4β7(+) Memory)=CD4(+), CD45RA(−), α4β7(+); CD4(+) T Cell (α4β7(−) Memory)=CD4(+), CD45RA(−), α4β7(−). Mean and SD from 3 individual healthy donors is shown, with 4–16 replicate wells per chemokine per donor (4 for SDF-1α and MIP-3β; 16 for TARC and MDC), and 24 wells for control lacking chemokines. To calculate specific migration, the mean number of cells/well that migrated into the bottom well in the absence of chemokine (background) was subtracted from the total number of cells/well that migrated to chemokine in parallel wells. To calculate the % representation of each lymphocyte subtype in the migrated populations, the number of specifically migrated cells/well belonging to each subtype was divided by the total number of specifically migrated cells/well.

The selective activity of the CCR4 ligands on circulating α4β7⁻ memory cells suggests a role in tissue-selective lymphocyte recruitment from the blood. To explore this possibility further, the responses of the two best-characterized, antigenically-defined tissue-targeted memory T cell subsets were compared. These subsets were intestinal ($α4β7^{hi}$) memory CD4⁺ cells, and skin homing memory CD4⁺ T cells defined by the cutaneous lymphocyte antigen, CLA. FIG. 2 shows the profile of peripheral blood lymphocytes from a typical healthy donor. CLA vs α4β7 staining of CD4(+)/CD45RA(−) memory lymphocytes from peripheral blood. Gates are drawn around the skin associated CLA(+)/α4β7(−) and intestinal CLA(−)/α4β7(+) memory subpopulations.

Figure 3:
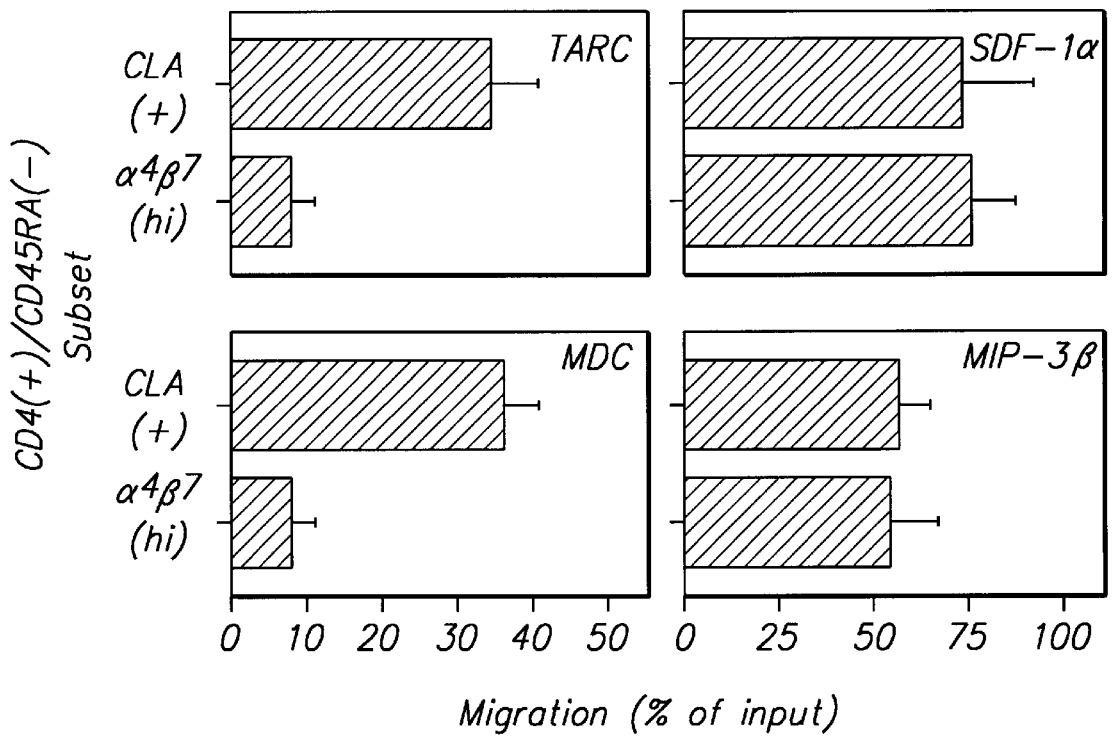
FIG. 3 illustrates the per cent migration of CLA(+)/α4β7(−) and CLA(−)/α4β7(+) memory subpopulations to various chemokines. Migration of human peripheral blood lymphocytes through 5 μm pores, FACs analysis.

CLA is a sialyl Lewis$^x$-related carbohydrate-dependent T cell epitope that identifies cutaneous memory cells and functions as a T cell homing receptor for skin. As shown in FIG. 3, TARC and MDC attract these skin homing memory cells extremely well, whereas intestinal $α4β7^{hi}$ memory T cells respond poorly. α4β7⁻ CLA⁻ T cells also migrated significantly, although consistently less well than the CLA⁺ population, suggesting that responsiveness of cutaneous memory lymphocytes for CCR4 ligands may be shared with a subset of other systemic memory cells.

The calculation of migrated cells and calculation of % migration in FIG. 3 were performed as described in Campbell et al. (1998), supra. Briefly, migration assays were carried out in RPMI-1640 with 0.5% BSA using 24-well plate tissue culture inserts (Costar Corp., Cambridge, Mass.) with 5 μm pore polycarbonate filters. 5×10⁵ cells were placed in the upper chamber in 100 μl, 600 μl of chemokine dilution in the lower well; and migration carried out for 90 min at 37° C. To calculate per cent migration, the number of cells of each subtype was determined for the starting population of each chemotactic assay. Next, the number of cells belonging to the same subtype was determined for the migrated population, and the per cent migration determined from these two numbers. Mean and SD from 6 individual experiments is shown (wells per experiment described in FIG. 1). Mean background migration of 1.07% for CLA(−)/α4β7(+) cells and 2.74% for CLA(+)/α4β7(−) cells has been subtracted. The difference in % migration between CLA(+)/α4β7(−) and CLA(−)/α4β7(+) is highly significant by the Mann-Whitney rank order test for TARC and MDC (p<0.01).

Consistent with these chemotactic responses, immunofluorescence staining confirmed differential expression of CCR4 on skin-associated vs. intestinal memory cells. As illustrated in FIG. 4, most CLA⁺ memory CD4 cells express very high levels of CCR4 (>95% positive; >70% over 100 mean fluorescence units), whereas most $α4β7^{hi}$ memory cells are weak or negative (<30% positive; 90% <100 mean fluorescence units). These data demonstrate that CCR4 and its ligands mediate preferential recruitment of α4β7⁻ systemic memory T cells, especially the skin homing population.

In FIG. 4, peripheral blood memory CD4(+) subsets were defined by four color flow cytometry as follows: CLA⁺ (left panel)=CD4(+), CLA(+), α4β7(−); CLA−/α4β7⁻ (center panel)=CD4(+), CLA(−), α4β7(−); $α4β7^{hi}$ (right panel)= CD4(+), CD45RA(−), α4β7(hi). Expression of CCR4 was determined by MAb 1G1 produced against CCR4-transfected mouse L1/2 cells essentially as described in Qin et al. (1996) *Eur. J. Immunol.* 26:640–647 and shown to specifically stain CCR4-expressing L1/2 cells but not control transfectants expressing other chemokine and related orphan receptors. Parallel staining with isotype-matched control IgG1 was negative for these subsets. Combined staining of three individual healthy donors is shown. Reagents: Chemokines were titered and used at the optimal concentrations for chemotaxis of unfractionated lymphocytes as follows: TARC, MDC and SDF-1α=100 nM, MIP-3β=1 μM. Synthetic human TARC and SDF-1α were obtained from Gryphon Sciences (South San Francisco, Calif.). Recombinant human MDC was obtained from Amgen (Boulder Colo.) and MIP-3β was purchased from PeproTech EC, Ltd. (Rocky Hill, N.J.). Directly conjugated antibodies used for FACs analysis were obtained from PharMingen, Inc. (San Diego, Calif.) unless otherwise indicated. FITC conjugated anti- CD3 (clone UCHT1), CD45RA (clone HI100), CLA (clone HECA 452, prepared by Butcher lab staff); PE conjugated anti- CD56 (clone B159), CD19 (clone B43), CD27 (M-T271), α4β7 (clone ACT-1, LeukoSite, Inc.); Biotinylated anti- CD45RA (clone HI100), CD16 (clone3G8), CD8 (clone RPA-T8); APC conjugated anti- CD4 (clone RPA-T4), CD8 (clone RPA-T8), CD56 (clone B159), TCRαβ (clone T10B9.1A-31). The second stage reagent used for all biotinylated antibodies was streptavidin-conjugated PerCP (Beckton Dickinson, San Jose, Calif.).

Chemokines may control lymphocyte trafficking not only through stimulation of chemotaxis, but also by triggering rapid integrin-dependent adhesion and arrest of lymphocytes on endothelium (Butcher (1991) *Cell* 67:1033–1036; Butcher & Picker (1996) *Science* 272:60–66). Consistent with this hypothesis, certain chemokines can trigger rapid arrest of lymphocytes under physiologic shear; and it is well documented that some chemokines can be expressed and/or presented by endothelial cells at sites of lymphocyte extravasation.

We have found that TARC can be expressed by activated endothelium. TARC, but not MDC, message was readily detected by Northern blot analyses in RNA from endotoxin- and cytokine-stimulated human umbilical vein endothelial cells; and TARC message was observed in primary cultures of enriched human tonsil HEV cells. Thus TARC can be expressed by endothelium, and therefore might be available for regulation of vascular interactions by lymphocytes.

The differential expression of CCR4 could contribute to lymphocyte recognition of cutaneous endothelium if TARC were displayed by venules in the skin. Immunohistological analyses of biopsies of chronically inflamed skin from patients with a variety of dermatologic disorders revealed reactivity of anti-TARC monoclonal antibody (MAb) with venules associated with lymphocyte recruitment, including (but not limited to) most E-selectin-expressing venules.

Frozen sections were fixed 10 min at RT in 4% paraformaldehyde in phosphate buffered saline (PBS). After washing in PBS, standard immunoperoxidase staining was performed as described by PickeretaL. (1991) Nature 349:796–800). MAb LS142-2D8 was produced against synthetic human TARC by standard techniques, and selected by ELISA for reactivity with TARC but not MDC or other chemokines.

Anti-TARC MAb (LS142-2D8) stains endothelial cells lining venules associated with lymphocyte infiltration in a case of psoriasis. Juxta-epidermal vessels were stained with anti-TARC but not with control IgG1 MAb. Venules in the dermis were also positive. In contrast, anti-TARC MAb did not stain a MAdCAM-1-positive venule in the colonic lamina propria. TARC reactivity was also observed in chronically inflamed skin in biopsies of lichen planus, atopic dermatitis and non-specific chronic inflammation.

Venules in minimally inflamed areas of the dermis were often positive as well, if less intensely and consistently. Reactivity was also observed on many high endothelial venules in inflamed tonsils. These vessels, thought to mediate recruitment of subsets of memory as well as naive lymphocytes, may express several chemokines to support interactions of diverse B and T cell subsets. In contrast, venules involved recruitment to gastrointestinal lamina propria (identified by MAdCAM-1 staining in biopsies of small and large intestine, stomach, and normal and inflamed colon) were usually negative; and reactivity when observed was focal and weak. Parallel immunohistological studies of macaque skin revealed scattered constitutive anti-TARC reactivity of venules, but with more extensive reactivity in experimentally induced delayed type hypersensitivity reactions, generated as described in Silber etal. (1994) *J. Clin. Invest.* 93:1554–1563. The results suggest that TARC is expressed in a regionally selective fashion by activated endothelium, and is well positioned to help control the vascular adhesion and arrest of circulating $CCR4^+$ lymphocytes on inflamed endothelium in skin.

It was then determined whether TARC could trigger rapid integrin activation and integrin-dependent arrest of circulating lymphocytes. In initial assays of rapid LFA-1-dependent lymphocyte adhesion to immobilized ICAM-1 in vitro, the CCR4 ligand TARC failed to induce adhesion of whole PBL that was detectable above background (Campbell et al. (1998) *Science* 279:381–384). However, purified $CD4^+$ lymphocytes displayed a significant response to TARC; and isolated $\alpha 4\beta 7^-$ memory $CD4^+$ lymphocytes demonstrated robust adhesion with up to 50% of input cells binding firmly to ICAM-1 within 2 mins. after chemokine addition (FIG. 5).

Moreover, TARC differentially triggered adhesion of skin vs. intestinal T cells. $CLA^+$ and $\alpha 4\beta 7^{hi}$ memory cells were enriched by binding isolated $CD4^+$ T cells to transfected fibroblasts expressing the CLA counter-receptor E-selectin, or the $\alpha 4\beta 7$ receptor MAdCAM-1, followed by elution with cation chelating buffer as previously described. As illustrated in FIG. 5, although both populations responded equally well to SDF-1, TARC selectively induced adhesion of the E-selectin-enriched $CLA^+$ population to ICAM-1. Interestingly, although a subset of $\alpha 4\beta 7^{hi}$ T cells do express CCR4, and $\alpha 4\beta 7^{hi}$ cells do migrate above backgorund to TARC (albeit very poorly), they display little or no rapid adhesion to ICAM-1: the low levels of CCR4 on the positive subset of intestinal memory cells (~7 fold lower median fluorescence than CLA+ T cells) may be insufficient to generate a robust proadhesive response, which typically requires engagement of large numbers of receptors.

Figures 5A, 5B, 5C:
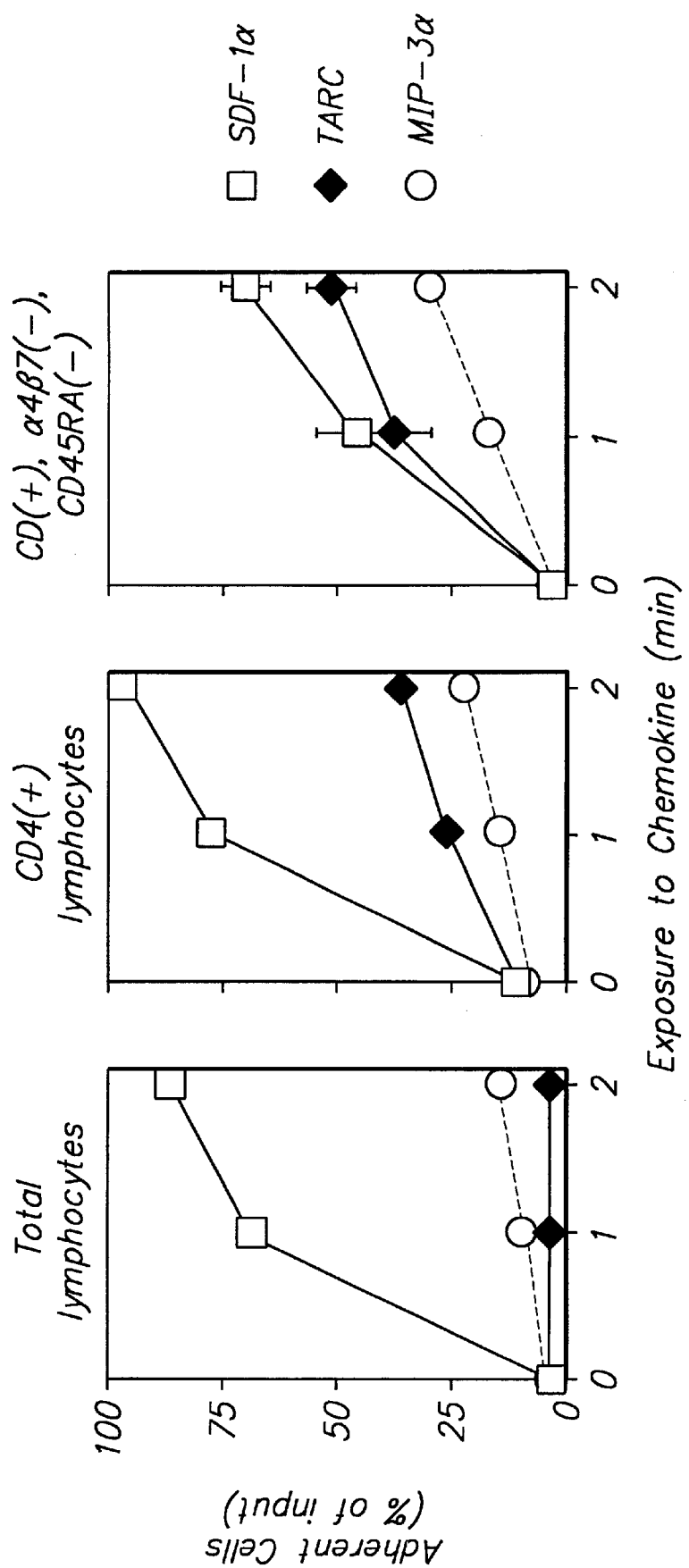
FIGS. 5A to FIG. 5C show TARC-induced rapid adhesion to ICAM-1 enriched in α4β7(−) memory CD4 cells.
Figure 6C:
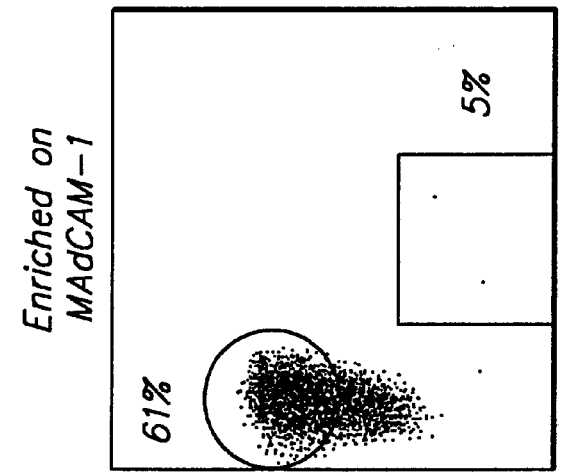
FIGS. 6A to FIG. 6C are plots of CLA(+) memory CD4 cells enriched by binding to E-selectin transfectants, and α4β7(hi) memory CD4 cells enriched by binding to MAdCAM-1 transfectants.
Figure 6B:
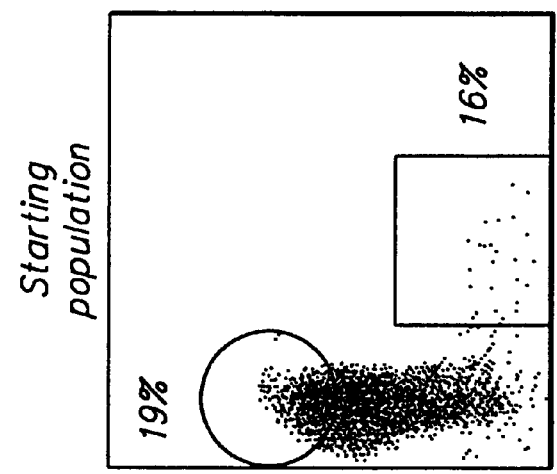
Figure 6A:
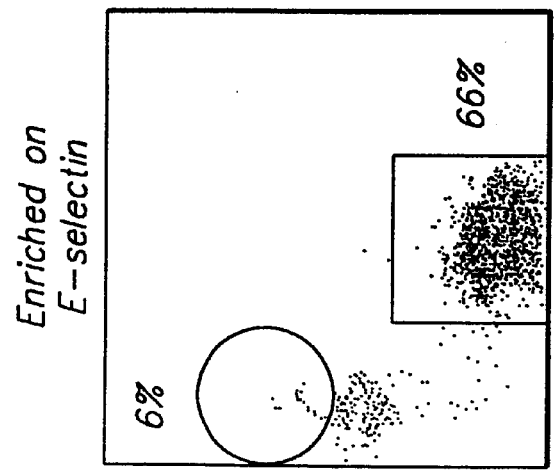

The static rapid adhesion assays shown in FIG. 5 were carried out as described in Campbell et al. (1998) *Science* 279:381–384. Briefly, human lymphocytes were allowed to settle in multiwell glass slides coated with ICAM-1 to a density of ~1000 sites per square micrometer. After cell settling, the indicated chemokines were added to a final concentration of 1 µM. The slides were washed at the indicated times to remove nonadherent cells, and bound cells were then fixed. Adherent cells in the microscopic field proximal to the site of chemoattractant addition were counted. Error bars indicate range of duplicate wells. Results are representative of experiments with two different donors. Test mononuclear cells were purified by density separation on ficoll, and either depleted of monoytes by incubation on plastic for direct use as unfractionated lymphocytes (left panel); or positively selected for CD4 expression (center and right panels). CD4(+) cells were purified from PBL with the use of anti-CD4 Dynabeads and the DETACH-a-BEAD system (Dynal, Lake Success, N.Y.) and used directly (center panel); or depleted of naive and $\alpha 4\beta 7(+)$ memory cells (right panel), by incubation with mouse anti-human CD45RA and mouse anti-human $\alpha 4\beta 7$ (unconjugated versions of the same MAbs used in FIG. 1), followed by microbeads coated with anti-mouse immunoglobulin, and magnetic depletion (Miltenyi Biotec, Auburn, Calif.). A portion of each processed cell population was stained with directly conjugated antibodies and analyzed by flow cytometry to ascertain purity. The CD4(+) population was 99% pure, and the CD4(+)/CD45RA(−)/$\alpha 4\beta 7$(−) population was 98% CD45RO(+) and 22% CLA(+). FIG. 6. Purified CD4 (+) T lymphocytes were incubated on MAdCAM-1 (CHO cells transfected with murine MAdCAM-1) or E-selectin (CHO-K cells transfected with human E-selectin, PDL, Inc.) in a T-175 at 370° C. for 30 min with occasional agitation, non-bound cells were washed away with warm complete medium, and bound cells were recovered by elution with divalent-cation-free HBSS for E-selectin or 0.5 mM EDTA for MAdCAM-1. Approximately 70% of the E-selectin-adherent population was $CLA^+$, and only 6% were $\alpha 4\beta 7^{hi}$ (with the remainder naive and $\alpha 4\beta 7^-$ memory cells); where cells enriched on MAdCAM-1 consisted of ~60% $\alpha 4\beta 7^{hi}$ cells and only ~5% $CLA^+$ cells. Data presented is representative of two individual experiments with different donors.

Figure 7:
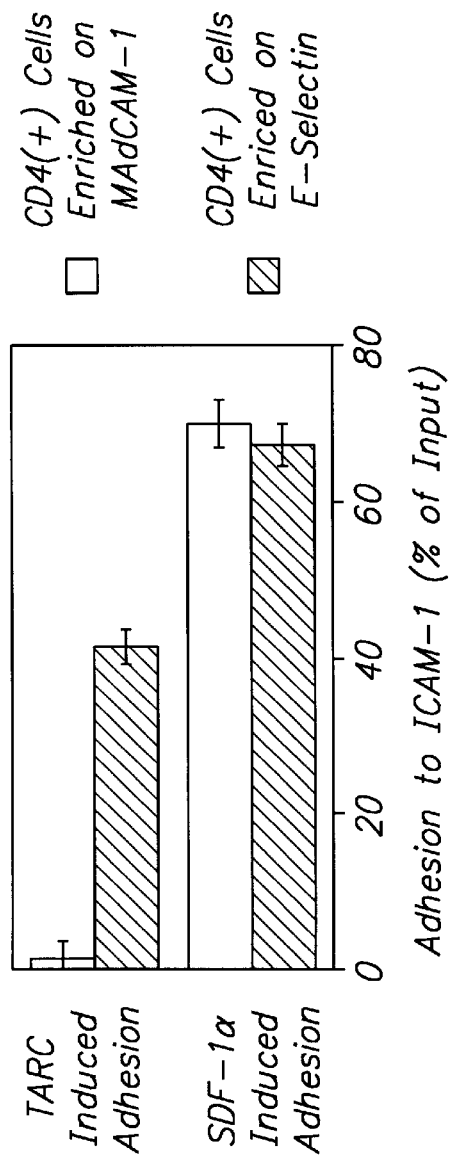
FIG. 7 is a graph illustrating that TARC triggers adhesion of skin-associated but not α4β7(hi) memory CD4 T cells to ICAM-1.

Enriched populations from above were tested for chemokine-induced adhesion to ICAM-1, shown in FIG. 7. Adhesion was assessed 2 min after chemokine addition. Background adhesion of 11% of input for E-selectin-enriched cells and 10% of input for MAdCAM-1-enriched cells was subtracted. Data shown are representative of 2 experiments (with different donors) with 2 duplicate wells for each data point. Error bars indicate range of duplicates.

Figure 8:
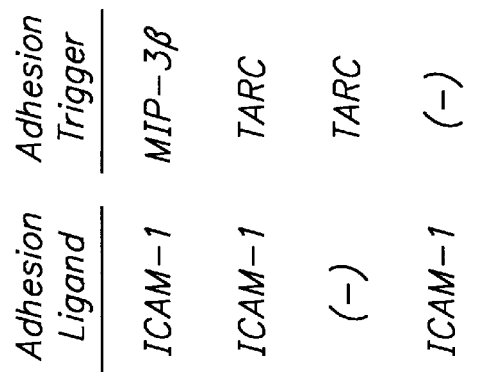
FIG. 8 is a graph demonstrating that TARC triggers rapid adhesion (<1sec) of human lymphocytes rolling on E-selectin under physiologic shear. Adherent lymphocytes accumulate on capillary tube walls under shear only when E-selectin, chemokine and ICAM-1 are all present.

Triggered adhesion of lymphocytes to endothelium in vivo must occur within seconds and under conditions of strong shear stress at the vascular wall. In inflamed skin, the vascular CLA receptor E-selectin is thought to mediate initial cell contact (tethering) and support rolling, and $\beta 2$ integrin ligands mediate arrest, with a variable contribution of $\alpha 4\beta 1$ integrin and VCAM-1 (Butcher & Picker (1996), supra.) Therefore, to determine whether the CCR4 ligand TARC could mediate activation-dependent arrest of lymphocytes rolling under physiologic conditions, we coated capillary tubes with E-selectin in combination with TARC and/or ICAM-1, and passed PBL through the tube at a wall shear stress of 2 dynes/cm². As illustrated in FIG. 8, many rolling lymphocytes came to a rapid stop. Arrest occurred within less than 1 second after initial rolling for most cells (FIGS. 9A and 9B), and required the combined presence of all three components: lymphocyte rolling was unperturbed in the absence of ICAM-1 or TARC, but arrest was dramatically less efficient (FIG. 8). We conclude that TARC can combine with vascular E-selectin and integrin ligands in a multi-step adhesion cascade in which both CLA/E-selectin and CCR4/TARC contribute to the selective arrest of skin homing T cells.

The adhesion assays under shear, shown in FIG. 8, were performed as described above. Briefly, cells at $2\times10^6$/ml were a passed through a capillary tube (1.025 mm inner diameter, Drummond, Broomall, Pa.) at 1250 µl/min (controlled by a Harvard 33 syringe pump, Harvard Apparatus, South Natick, Mass.), which generates a wall shear stress of ~2.0 dynes/cm². Adherent cells were counted in 10 fields (fields recorded at 30 sec intervals) between 6 and 11 min after the start of the assay. Combined data for 4 different healthy donors (10 fields each) is shown. Error bars indicate SD. The difference in cell accumulation between tubes coated with E-selectin, TARC and ICAM-1 and tubes missing either TARC or ICAM-1 was highly significant for the four donors by the Mann-Whitney rank order test ($p<0.03$). Human E-selectin was purified from E-selectin-transfected L1/2 cells on an affinity column of monoclonal antibody E8. 16-3 (PDL, Inc.) conjugated to Sepharose, using the tissue lysis procedure previously described (Honda et al. *J. Immunol.* (1994) 152:4026–4035). ICAM-1 was prepared from mouse spleen and lymph nodes as described in Campbell et al. (1998), supra. Detergent-solubilized adhesion molecules (ICAM-1 and E-selectin) and chemokines were coated on the inner surfaces of the tubes as previously described (infra.)

Figure 9B:
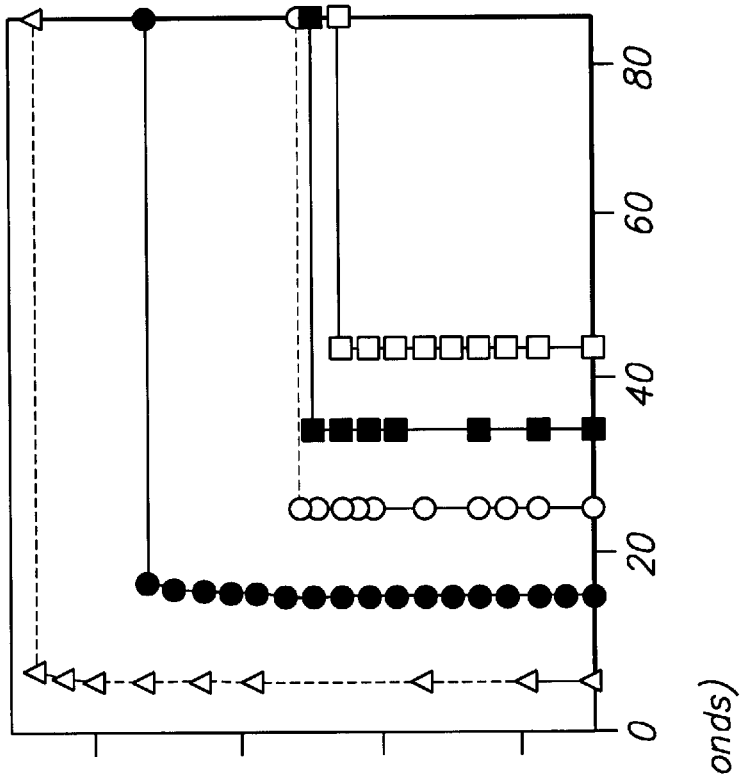
FIG. 9A and FIG. 9B demonstrate that TARC-induced ICAM-1 adhesion of lymphocytes rolling on E-selectin is extremely rapid.
Figure 9A:
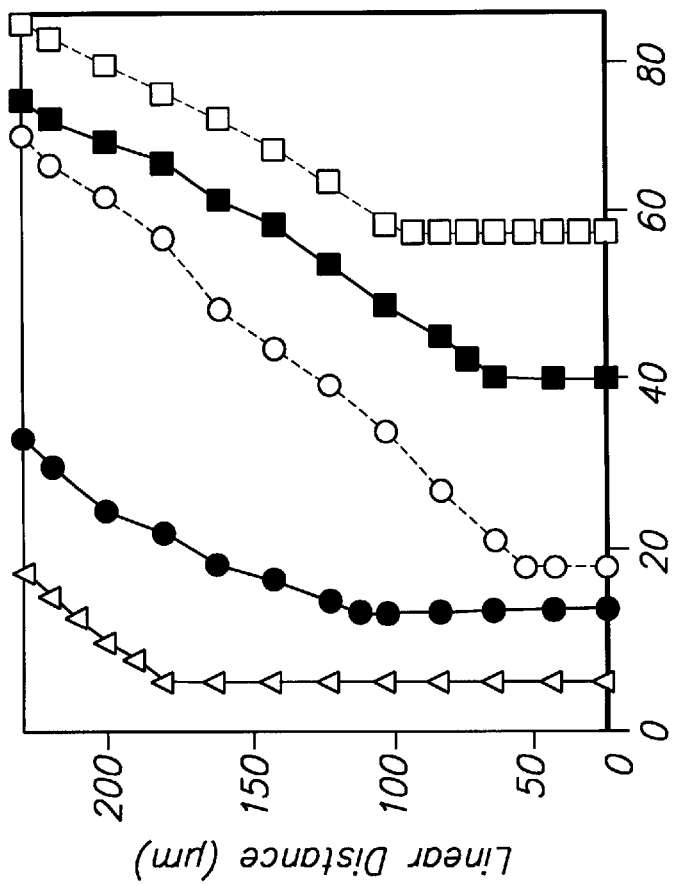

FIG. 9 shows the plots depicting behavior of individual cells interacting with the coated areas of capillary tubes, as described above. Each line represents a cell that began interaction with the coated adhesion molecules within the field of observation. The slope of the line is proportional to the velocity of the cell. The behavior of 5 representative cells is shown for each assay. The y axis indicates the length of the microscopic field (220 µm), with zero as the entry into the field and 220 as the downstream exit from the field. The depicted time at which the cell enters the field is arbitrary. Capillary tubes were coated with a combination of E-selectin and ICAM-1 plus either medium alone (FIG. 9A) or TARC (FIG. 9B). The mean velocity of tumbling cells was 327µm/sec (+88 SD) under these conditions, determined for 10 randomly chosen cells on uncoated areas of the capillary. The mean velocity of rolling cells was 5.1 µm/sec (+1.9 SD), determined for 10 randomly chosen cells on E-selectin+ICAM-1 (without TARC). The deceleration time was defined as the time elapsed between the point at which the cell's speed dropped two standard deviations below the mean tumbling velocity (327−176=151 µm/sec) and the point at which the cell came to a complete stop. The mean deceleration time was determined for 13 cells that remained arrested for >1 min, and was 0.87 sec (+0.92 SD). The longest deceleration was 2.51 sec for a cell that initially arrested, then rolled another cell length before coming to complete arrest. The fastest deceleration time was <0.03 sec, the duration of a VHS video frame, which was observed for 3 of the 13 cells.

Recent reports have suggested a role for CCR4 and its ligands, especially MDC, in selective chemotaxis of in vitro-polarized Th2 T lymphocytes. However, CLA$^+$ T cells are not enriched in Th2 cells. In fact, upon short term stimulation with general activating stimuli, essentially identical fractions of blood memory CLA$^+$ and CLA$^-$ CD4 cells display Th1 vs. Th2 cytokine profiles.

The above data demonstrates that, on circulating memory lymphocytes, CCR4 functions as a chemoattractant "homing receptor" for skin and potentially other non-intestinal tissues, independent of cytokine commitment patterns. Its differential expression and function on fully polarized Th2 vs. Th1 cells in vitro may imply a parallel role for the relatively infrequent effector Th2 cells that enter the blood, or may be more relevant to the behavior of activated effector T cells within extravascular sites of inflammation.

In conclusion, TARC and its lymphocyte receptor CCR4 are involved in the homing of circulating memory T cells, and in their interactions with vascular endothelium in cutaneous sites of inflammation. They provide the first evidence for chemokine involvement in tissue-selective lymphocyte-endothelial recognition, and suggest that CCR4 and its ligands play a fundamental role in the regional targeting of memory T cells, and thus in the functional segregation of intestinal vs. systemic, especially cutaneous, immune responses.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of modulating the trafficking of integrin α4β7⁻, CD45Ra⁻ CD4⁺ systemic memory T cells in a mammalian host, the method comprising:

administering an effective amount of a CCR4 modulating agent, in a dose effective to modulate said trafficking of integrin α4β7⁻ systemic memory T cells.

2. The method of claim 1, wherein said administration provides for a prolonged localized concentration of said CCR4 modulating agent.

3. The method of claim 1, wherein said systemic memory T cells are further characterized as CLA⁺.

4. The method of claim 3, wherein said localized concentration of said CCR4 modulating agent is cutaneous.

5. The method of claim 1, wherein said CCR4 modulating agent is a CCR4 agonist.

6. The method of claim 5, wherein said CCR4 agonist is selected from the group consisting of thymus and activation-regulated chemokine TARC and macrophage-derived chemokine MDC.

7. The method of claim 1, wherein said CCR4 modulating agent is a CCR4 antagonist.

8. The method of claim 7, wherein said CCR4 antagonist is an antibody.

9. The method of claim 8, wherein said antibody is a monoclonal antibody.

10. A method of modulating the trafficking of integrin α4β7⁻, CD45Ra⁻ CD8⁺systemic memory T cells in a mammalian host, the method comprising:

administering an effective amount of a CCR4 modulating agent, in a dose effective to modulate said trafficking of integrin α4β7⁻ systemic memory T cells.

11. A method of modulating the trafficking of CCR4+ skin homing leukocytes, wherein said leukocytes are integrin α4β7⁻, CD45Ra⁻ CD4⁺ systemic memory T cells, to cutaneous tissue or skin, the method comprising:

administering an effective amount of a CCR4 modulating agent, wherein said agent modulates the interaction between CCR4 and a ligand.

12. A method of treating inflammatory skin disease, the method comprising:

administering to a patient an effective amount of a CCR4 antagonist, wherein said CCR4 antagonist interferes with the interaction between CCR4 present on a integrin α4β7⁻, CD45Ra⁻, CD4+ systemic memory T cell and a ligand, wherein said CCR4 ligand is thymus and activation-regulated chemokine TARC or macrophage-derived chemokine MDC.

13. The method according to claim 12, wherein said CCR4 antagonist is an antibody.

14. The method according to claim 13, wherein said antibody binds to CCR4.

15. The method according to claim 13, wherein said antibody binds to a CCR4 ligand.

* * * * *